(12) United States Patent
Boeck et al.

(10) Patent No.: US 8,562,801 B2
(45) Date of Patent: Oct. 22, 2013

(54) ELECTRODE WITH INTEGRATED OPTICAL SENSOR

(75) Inventors: Christian Boeck, Kappel a.A. (CH); Martin Heule, Birmensdorf (CH); Stefan Berger, Burgdorf (CH)

(73) Assignee: Metroglas AG, Affoltern a/A (CH)

( * ) Notice: Subject to any disclaimer, the term of this patent is extended or adjusted under 35 U.S.C. 154(b) by 275 days.

(21) Appl. No.: 13/055,331

(22) PCT Filed: Jul. 22, 2008

(86) PCT No.: PCT/EP2008/059594
§ 371 (c)(1),
(2), (4) Date: Apr. 18, 2011

(87) PCT Pub. No.: WO2010/009759
PCT Pub. Date: Jan. 28, 2010

(65) Prior Publication Data
US 2011/0186447 A1     Aug. 4, 2011

(51) Int. Cl.
*G01N 27/333*     (2006.01)
*G01N 27/403*     (2006.01)
*G01N 21/01*     (2006.01)

(52) U.S. Cl.
USPC ........................................................ 204/433

(58) Field of Classification Search
USPC ................... 422/82.05–82.11; 600/309–344; 204/416–418, 420, 430
See application file for complete search history.

(56) References Cited

U.S. PATENT DOCUMENTS

| | | | |
|---|---|---|---|
| 4,494,003 A | 1/1985 | Hager et al. | |
| 5,043,286 A | 8/1991 | Khalil et al. | |
| 5,596,988 A * | 1/1997 | Markle et al. | 600/353 |
| 6,602,716 B1 | 8/2003 | Kliment | |
| 2002/0025547 A1 | 2/2002 | Rao | |
| 2008/0275428 A1* | 11/2008 | Tegg et al. | 604/533 |
| 2009/0075321 A1* | 3/2009 | Obeid et al. | 435/29 |

FOREIGN PATENT DOCUMENTS

| | | |
|---|---|---|
| DE | 4121397 | 1/1993 |
| EP | 0104619 A2 * | 4/1984 |
| EP | 0709669 | 5/1996 |
| EP | 1921439 | 5/2008 |
| WO | WO 2007110890 A2 * | 10/2007 |

OTHER PUBLICATIONS

EPO computer-gnerated Englsih language translaiot of the Description of Diehm et al., EP 0709669 A1, translation generated on Mar. 12, 2013.*
EPO computer-gnerated Englsih language translaiot of the Claims of Diehm et al., EP 0709669 A1, translation generated on Mar. 12, 2013.*
Bambot et al., "Phase Fluorometric Sterilizable Optical Oxygen Sensor", Biotechnology and Bioengineering, Vo. 43, pp. 1139-1145, 1994, John Wiley & Sons, Inc., XP-000921111.

* cited by examiner

*Primary Examiner* — Alex Noguerola
(74) *Attorney, Agent, or Firm* — Shoemaker and Mattare

(57) ABSTRACT

Glass pH electrode with integrated optical sensor, characterized in that said electrode can be sterilized without substantial alteration of its optical characteristics, in particular in respect to gamma ray irradiation sterilization.

17 Claims, 6 Drawing Sheets

Figure 1:
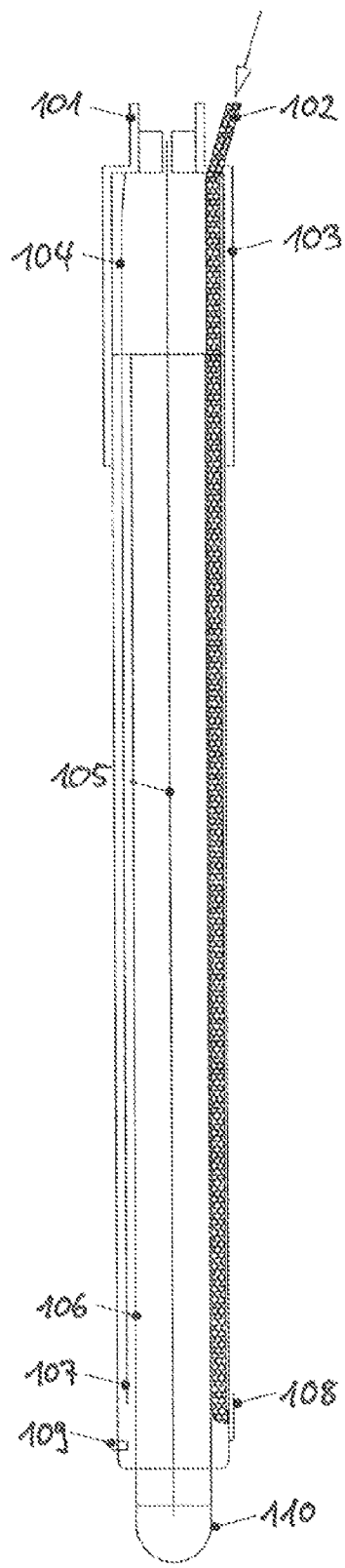

Fig. 2a:
Fig. 2b:
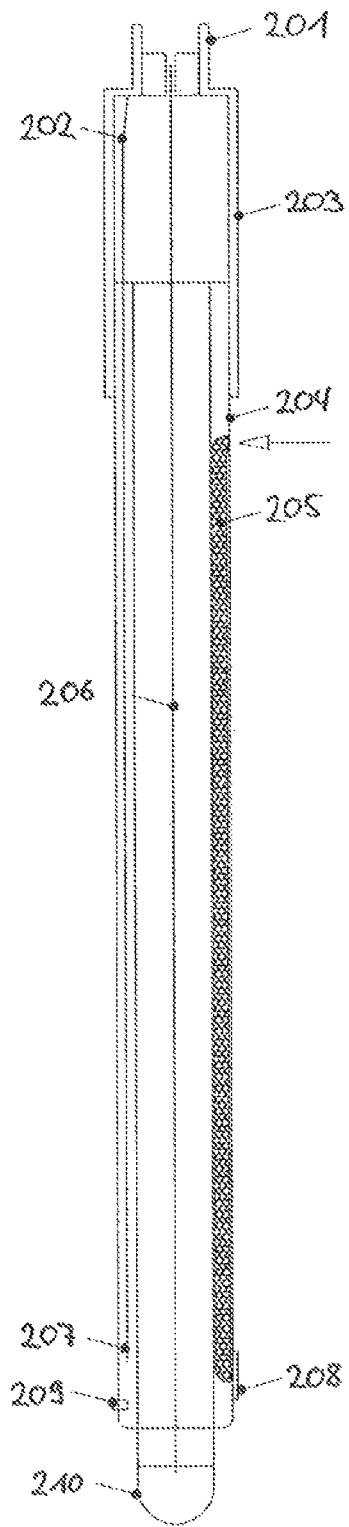
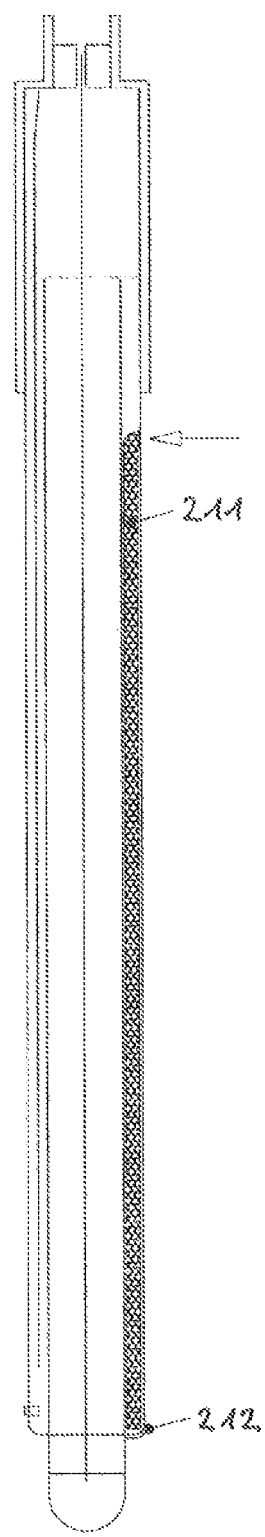

ELECTRODE WITH INTEGRATED OPTICAL SENSOR

The present invention relates to the field of pH sensors, especially pH glass electrodes, combined with a second sensor.

There is a strong need in the field of biotechnology and related pharmaceutical applications to monitor physical and chemical parameters such as pH, dissolved oxygen, turbidity and many more.

For measuring pH, combined glass electrodes are abundantly used in the field and are available from a variety of manufacturers.

For measuring dissolved oxygen, electrochemical sensors based on the well-known Clark principle are frequently used. In brief, a membrane limiting the diffusion of oxygen is brought in close contact with a cathode that reduces oxygen to water. The limited diffusion of oxygen across the membrane leads to a stable reduction current that is proportional to the oxygen partial pressure on the outside of the membrane. The electrochemical Clark-type sensor needs to be calibrated by performing a measurement. More recently, alternative sensors based on fluorescent properties of chemical compounds that interact with oxygen have been suggested.

Moreover, there are optical sensors for pH, oxygen saturation and other parameters available. U.S. Pat. No. 6,602,716 B1 teaches a sensor system suitable for optical determination of pH, $CO_2$ and ionic compounds based on the decay times of luminescent complexes that change when the complex is brought in contact with a certain activity of analyte molecules. Typically, these complexes are embedded in an organic matrix and are therefore very well suited to be embedded in a polymer matrix. Polymers can also be obtained cheaply and therefore fulfil criteria for cost efficiency. Often, the sensitive polymer is provided for instance as a simple silicone material that can be cast or glued to a multitude of surfaces. This allows employing many of such chemical sensors as are disclosed in US 2002/0025547 (Rao).

In addition to the ease of application, the optical properties of the aforementioned optical sensors are stable for years, allowing to pre-calibrate the optical sensors for dissolved oxygen before actually delivering them to the customer. The customer therefore does not have to calibrate by performing an actual measurement. The knowledge of the pre-determined optical response function is sufficient to calibrate the system.

In principle, there are two main approaches to deliver the excitation light and to collect the response signal. One is to place the light source (usually a light emitting diode, LED) and the photodetector close to the optical sensor. The second option is to guide the light from the source to the sensor by (an) optical fibre(s). The response signal can be collected using the same or (a) separate fibre(s).

In the biotechnological industry, polymer optical fibres (POF) of 2 mm internal diameter are abundantly used. Whereas the optical sensors for dissolved oxygen available today are able to reach similar measurement quality as the electrochemical Clark sensors, the optical pH sensors lack the wide dynamic range of pH glass electrodes by orders of magnitude. Furthermore, the fluorescent properties can also be influenced by matrix effects such as variations due to differing ionic strength or temperature changes. For high precision applications it is therefore indispensable to take these matrix effects into account when calibrating the system. Glass membranes, however, do not show such a distinct matrix effect even at high precision requirement levels and the temperature dependence is well understood by the Nernst equation.

Biotechnology requires that the sensors are sterilised before using them e.g. in a fermentation process or in a sensitive bioprocess production step. Two sterilisation methods are predominantly used:

In the case of fixed installations, e.g. steel bioreactors, steam sterilisation (autoclaving) is used. Typical conditions include steam temperatures of up to 140° C. for at least 20 min and an increased pressure of 2 bar. Larger vessels are usually equipped with a system allowing the steam sterilisation of the inside as a built-in function (steam-in-place systems). Smaller vessels are usually transferred into an autoclave for steam sterilisation.

In the case of more recently introduced single use bioprocess systems, irradiation by gamma rays is frequently used to sterilise single use equipment. This has the advantage that fully packaged assemblies can be sterilised without subjecting them to excessive heat, moisture and pressure, and that closed volumes can be sterilised as well, whereas steam sterilisation only works on surfaces that are exposed to the steam conditions. However, commonly known optical waveguide arrangements are not made to be sterilizable by e.g. gamma rays.

Further sterilisation methods used in the field include e-beam treatment of surfaces or treatment by chemicals such as ethylene oxide.

The object of the present invention is thus to overcome the above-mentioned drawbacks of the prior art, more particular to provide a reliable combination of a pH electrode with a wide dynamic range and an optical sensor, preferably for dissolved oxygen, and which combined sensor is advantageously usable in biotechnology.

Towards this end, an electrode according the invention is provided, which comprises
  i) a pH glass electrode for measuring the pH of an analyte; and
  ii) an optical sensor for measuring a physical and/or chemical property of an analyte, wherein the physical and/or chemical property is not the pH.

The electrode is sterilizable without significant alteration of the optical characteristics of
  the optical input- and output path(s) to and from the optical sensor; and
  of the optical sensor itself.

The combined sensor according to the invention is useable to carry out two different measurements, in particular simultaneously. Measurement of the pH value is done with the pH glass electrode, while yet another physical and/or chemical property, preferably the dissolved oxygen content of the sample solution, is done with an optical sensor. The electrode according to the present invention is also sterilizable. This is very favourable for use of the electrode in single use bioprocess systems, since the full installation including the electrode can now be easily sterilized, especially by means of irradiation with gamma rays. Preferably, it withstands both gamma ray irradiation and steam sterilisation, and retains its full measurement capability after the sterilisation procedure. Gamma radiation is more intended for sterilising a sensor before use and using it as a disposable equipment for example for single-use biotechnology equipment. Steam sterilisation is geared more towards using the sensor multiple times.

Here and henceforth, "significant alteration of the optical characteristics" is understood as
  i) any change (reduction or increase) of light transmittance $(I/I_0)$ in the wavelength range of 400 nm to 600 nm by more than 10% of the original light intensity coupled into the optical system; and/or ii) the emergence of a new, previously not present fluorescent signal upon irradiation with UV light in the wavelength range of 200 nm to 600 nm.

Thus, filtering effects due to changes of material characteristics caused by the sterilisation method of the waveguide material itself or its cladding or any other component able to interact with the sensing light that would interfere with the measurement method are preferably excluded. Such interference i) or ii) typically causes an optical sensor response to deviate quantitatively by more than 0.5% compared to its state before applying the sterilisation process in question. A good example is the sensor response for dissolved oxygen given in units of percentage of a fully oxygen-saturated medium. A deviation by more than 0.5% would not be acceptable.

There are five basic optical chemical sensing techniques that can also be used in the context of the present invention: measuring absorbance, fluorescence intensity, ratiometric fluorescence, fluorescence lifetime and fluorescence polarization. A culture parameter such as dissolved oxygen can be measured using any of the five techniques, however, the preferred technique is fluorescence lifetime. Optical density is measured via absorbance. Fluorescence lifetime is relatively immune to leaching, photobleaching, excitation light intensity and other artefacts which may affect fluorescence measurements. In fluorescence lifetime measurements for oxygen for instance, a suitable oxygen-quenched luminophore is excited with modulated light and the lifetime (average time between absorption of a proton and the resultant fluorescence emission) is measured by determining the phase shift between the excitation light and the emission. As noted above, the excitation source produces light which excites the optical sensor. The excitation source employed is preferably a light-emitting diode (LED) that emits light at a wavelength that corresponds to the excitation wavelength of the chemical sensor. For example, a blue LED and an UV LED are preferably used to measure pH when using a chemical sensor such as a 530 nm photodetector. A blue LED can also be used to measure dissolved oxygen when using a 590 nm photodetector. A red LED can be used to measure optical density. The detector employed to detect the luminescence emitted from or light absorbed by the optical sensor can be a photodetector, spectrometer and/or diode array, photomultiplier tube (PMT), charge coupled device (CCD) camera, semiconductor photoreceiver or other detector known in the art. The design wavelength of the detector used is preferably matched to the luminescence wavelength of the respective chemical sensor. For example, if photodetectors are employed, a 590 nm photodetector can be used to measure the luminescence from a dissolved oxygen sensor and a 600 nm photodetector can be used to measure optical density. A pass filter or emission filter may be optionally positioned between each chemical sensor and its respective detector to block wavelengths other than the luminescence wavelength of the chemical sensor. Dissolved oxygen sensors include, but are not limited to, ruthenium-based oxygen sensing films such as Ru(II) tris (4,7-diphenyl-1,10-phenanthroline) complex, immobilized in a silicone rubber membrane (Bambot, S. B. et al, Biotechnol Bioeng. 43: 1139-1145 (1994)). As an alternative, ratiometric oxygen measurement based on a new class of compounds that show dual emission peaks, an oxygen insensitive and an oxygen sensitive one, can be employed. Such compounds include, but are not limited to, heterocyclic-substituted platinum 1,2-enedithiolates such as BPh4 ((dppe)Pt{$S_2C_2(CH_2CH_2$—N-2-pyridinium)}, wherein "dppe" is 1,2-bis(diphenylphosphino) ethane) (Kostov, Y. et al., Appl. Spectroscopy 54: 864-868 (2000)). By measuring the ratio of the two emission peaks, the skilled artisan can quantify the ambient oxygen tension around the chemical sensor (Kostov, Y. and Rao, G., Rev. Sci. Inst. 70: 4466-4470 (1999)).

In luminescent quenching, dissolved oxygen is detected using frequency domain detection of the fluorescence lifetime of a ruthenium porphyrin, for example, wherein the excitation light is modulated and the lifetime is measured by determining the phase shift between the modulated excitation light and the resulting modulated fluorescence emission. This is a well-established method of oxygen detection (Bambot, S. B. et al, Biotechnol. Bioeng. 43: 1139-1145 (1994)) and relies on the reversible quenching of fluorescence emission due to oxygen binding. Its greatest advantage is that the measurements are equilibrium based and do not consume oxygen.

According to a preferred embodiment, said optical characteristics of the optical input- and output path(s) to and from the optical sensor and of the optical sensor itself is the spectrum in the range of about 200 nm to about 800 nm, preferably in the range of about 350 nm to about 700 nm, most preferably in the range of about 400 nm to about 650 nm. In order to allow for the optical measurements, the light transmittance preferably is as high as to allow the incident light to be provided by a standard LED and the recollection of fluorescence light by commonly available electronic photodetector components; thus, according to the preferred embodiment, resorting to high intensity light sources and highly sensitive and therefore expensive detectors is not necessary.

In another preferred embodiment the optical sensor is mounted on the outside of the electrode shaft, preferably on the lower-third of the electrode shaft.

When the optical sensor is mounted on the outside of the electrode shaft, preferably on the lower-third of the electrode shaft, the pH glass, the reference junction of the pH electrode and the optical sensor can be brought in contact with the solution to be measured at the same time.

Preferably, the optical input- and output path(s) to and from the optical sensor comprise an optical waveguide, functionally connected or connectable to the optical sensor. Such optical waveguide is advantageously integrated in the electrode shaft.

In comparison to the use of a Clark-type sensor together with a pH glass electrode, the proposed combined electrode has the advantage that it essentially takes the shape of a pH glass electrode. In the former case, there would have to be two distinct sensor entities, each with its own reference cell, and individual membrane fixation. The combination of a pH glass electrode into one housing together with a Clark-type sensor would thus have only limited advantages compared to using two individual sensors.

In another embodiment of the invention, the optical waveguide is displaceable from the electrode. This allows for easy replacement of the waveguide it this is necessary, either because it is damaged, or because other optical and/or chemical properties of the waveguide are desired for a specific purpose. Most advantageously, the waveguide can be displaced e.g. from the electrode before sterilization, in order to prevent any change of the optical characteristics of the waveguide due to the sterilization process. Even when the electrode is already installed in a bioprocess system, the interior of the whole bioprocess system remains sealed with the optical waveguide being displaced.

In a preferred aspect of the invention said electrode is sterilizable by
i) steam sterilisation; and/or
ii) chemical sterilisation; and/or
iii) irradiation sterilisation;

without significant alteration of the optical characteristics in the optical path(s) of and/or to the optical sensor. Preferably, the electrode is sterilizable by irradiation sterilization chosen from the group consisting of gamma ray irradiation, electron beam processing, treatment with X-ray, treatment with UV light, and combinations thereof; without significant alteration of the optical characteristics in the optical path(s) of and/or to the optical sensor.

Steam sterilisation typically includes heating to 120 to 140° C., 2 bar pressure for at least 20 min. However, protocols that differ from these most commonly used values depending on application-specific needs such as materials sensitivity to heat etc.

Most preferably, the electrode is sterilizable by treatment with gamma rays at doses preferably ranging from 10 to 100 kGy, most preferably at doses ranging from 25 to 50 kGy, without significant alteration of the optical characteristics in the optical path(s) of and/or to the optical sensor.

The optical properties of the materials used must therefore not be affected adversely by this process. In the case of polymers there are several possibilities, for instance to use polycarbonate compositions as discussed in EP 394 778 by Lundy and Krishnan and references therein. It is discussed extensively that polycarbonates yellow during the irradiation process. By means of a stabilising agent it is tried to minimize the yellowing effect. A polycarbonate resin thus resistant to yellowing and haze formation is a suitable material for the optical waveguide according to the present invention.

In an embodiment of the present invention the optical input- and output path(s) to and from the optical sensor, preferably the optical waveguide in said optical input- and output path(s) to and from the optical sensor, is made from a glass material.

Probably because of the wide availability of polymer materials and its compatibility to most of the fluorescent or luminescent molecules, the usage of glass has been overlooked. Glass is known for its high transparency over a very wide wavelength range, chemical stability, biocompatibility and would provide a suitable medium for transferring optical signals. The whole shaft of the electrode can be produced from a suitable glass, or, preferably, only relevant sections (e.g. a window) in the optical path can be produced from a suitable glass, for cost reasons. Glass is easy and robust to mount with a common adhesive and its surface can easily be chemically functionalised with the optical sensor. For example, a common polymer-based sensor patch can be fixed onto the glass, or the glass itself can be directly functionalized with e.g. luminescent molecules and/or complexes. Glass is also a thermally insulating material, which in the context of the present invention helps to establish thermal equilibrium of the optical sensor with the surrounding medium quickly. In addition, it can be sterilised by many methods, including steam, e-beam and by exposition to chemicals such as ethylene oxide. However, commonly used types of glasses are colorised when subjected to gamma ray sterilisation. Depending on the chemical elements present in the glass, a brown or purple color is often obtained. These properties are discussed for instance in U.S. Pat. No. 4,494,003 where glass is used as a detector for gamma radiation by measuring the change in color.

Advantageously, the glass of the electrode, especially the glass in the optical input- and/or output path(s) to and from the optical sensor, preferably the glass of the optical waveguide (102, 205, 211, 405, 505) in said optical input- and output path(s) to and from the optical sensor (108, 208, 212, 307, 416, 508) is or comprises a borosilicate glass containing cerium.

For the packaging of highly sensitive vaccines, glass ampoules resistant to gamma rays are known. For this very special application, there are special types of glass in use that do not exhibit any significant discoloration reaction upon exposure to gamma rays. A typical example of such a glass is NSV-51 borosilicate glass with cerium that is sold by Wheaton (Wheaton Glass Warehouse, Millville, N.J., USA). It is also a highly resistant type I glass suited for highest quality pharmaceutical applications. Other suitable glasses include quartz glasses and other glasses with low metals content may be suitable as well.

According to a preferred embodiment of the present invention, such type of glass is used at least for all glass parts of the electrode that are part of the optical path. This allows the optical path to retain a sufficiently high transparency and stability in color that allows for reliable optical measurements even after the gamma sterilisation procedure.

Alternatively it is possible to use this type of glass for all glass parts of the electrode, except for the pH-sensitive membrane glass which has its own special composition. There are known pH membrane glass types whose discolouring reactions do not adversely effect the formation of the electrochemical pH potential. Since membrane glasses are usually thinner than 1 mm, it is also possible to transfer light across the pH glass membrane without significant altering of the optical characteristics.

Another aspect of the invention concerns a bioreactor, preferably a single-use bioreactor, equipped with an electrode according to the invention, as outlined above.

Yet a further aspect of the invention pertains to a method of determining the pH and yet another physical and/or chemical property of an analyte, whereby an electrode according to the invention is used, as outlined above.

A further aspect of the present invention is the use of a material that is sterilizable without significant alteration of the optical characteristics of the optical input- and/or output path(s) to and from the optical sensor; and of the optical sensor itself; for the manufacture of an electrode according to the invention, in a preferred embodiment for the manufacture of a waveguide in the optical input- and output path(s) to and from the optical sensor of an electrode according to the invention. Such material is preferably a borosilicate glass containing cerium.

The present invention is described in even more detail by means of preferred embodiments and accompanying figures, without intending to limit the invention to theses specific embodiments.

FIG. 1: Electrode with optical waveguide

101 electrical connector, 102 optical waveguide, 103 sensor head, 104 reference wire, 105 internal reference wire (pH), 106 inner glass tube, 107 reference electrode, 108 optical sensor (in the form a material attached to glass containing the chemically sensitive fluorophore or luminophore), 109 diaphragm or liquid junction, 110 pH glass membrane FIG. 2a: Electrode with differently arranged optical waveguide FIG. 2b: Electrode with differently arranged optical waveguide and alternative sensor placement

201 electrical connector, 202 reference wire, 203 sensor head, 204 shaft glass tube, 205 optical waveguide, 206 internal reference wire (pH), 207 reference electrode, 208 optical sensor, 209 diaphragm or liquid junction, 210 pH glass membrane, 211 optical waveguide, 212 optical sensor.

Figure 3:
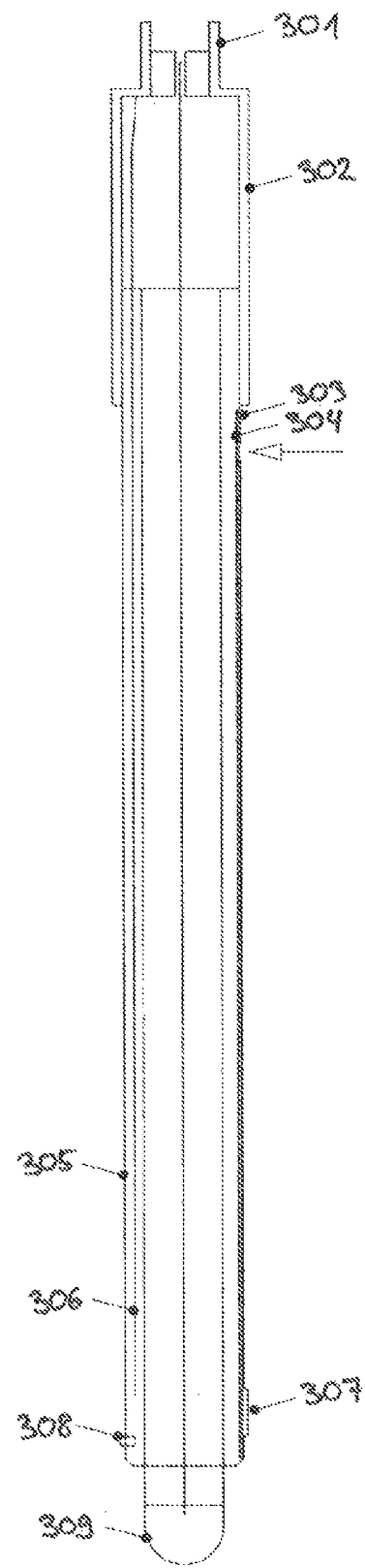

FIG. 3: Electrode with waveguide integrated in the outer shaft glass

301 electrical connector, 302 sensor head, 303 outer cladding/optical insulation on shaft glass, 304 inner cladding/ optical insulation on shaft glass, 305 shaft glass, 306 reference electrode, 307 optical sensor, 308 diaphragm or liquid junction, 309 pH glass membrane.

Figure 4:
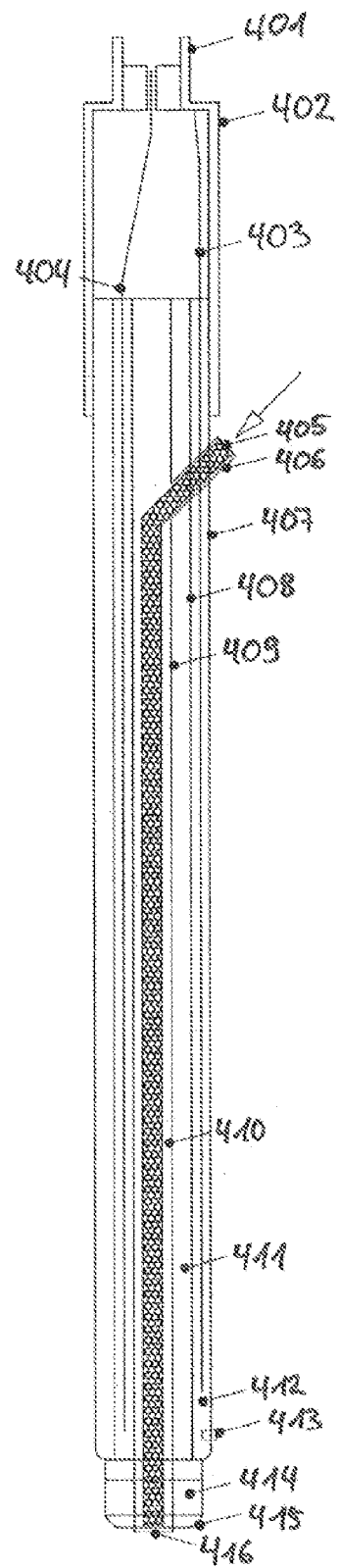

FIG. 4: Electrode with displaceable waveguide

401 electrical connector, 402 sensor head, 403 reference wire, 404 internal reference wire (pH), 405 optical waveguide (removable), 406 access to inner compartment (410), 407 shaft glass, 408 inner tube forming the chamber for the pH electrode, 409 inner tube forming the chamber for the optical waveguide, 410 inner optical waveguide compartment, 411 pH electrode compartment, 412 reference electrode compartment, 413 diaphragm or liquid junction, 414 pH glass membrane, e.g. formed as a cylinder, 415 bottom glass support, 416 optical sensor.

Figure 5:
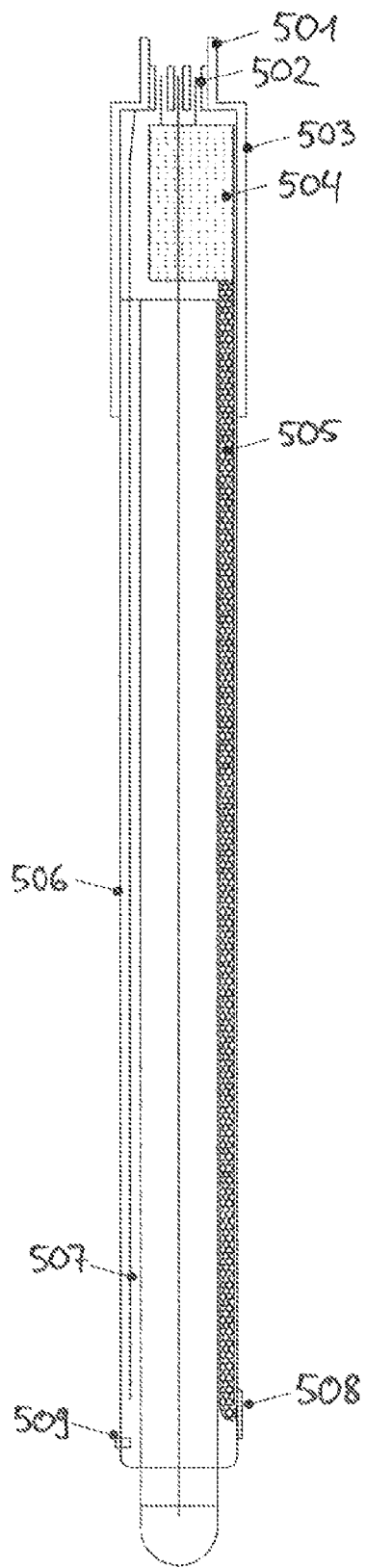

FIG. 5: Electrode with integrated opto-electronics

501 electrical connector, 502 connectors for the opto-electronic package, power and data transmission, 503 sensor head, 504 integrated opto-electronics for reading out optical sensor, 505 waveguide, 506 shaft glass, 507 reference electrode, 508 optical sensor, 509 diaphragm or liquid junction.

Figure 6:
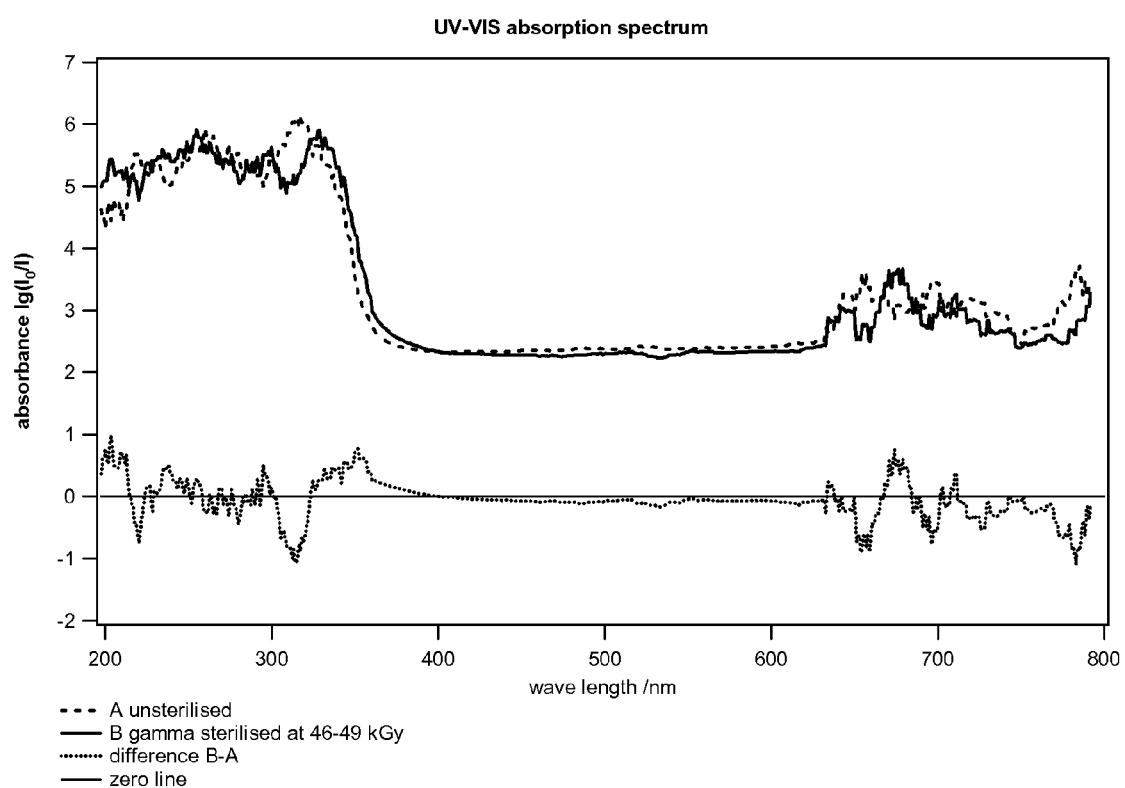

FIG. 6: Absorption spectra of two gamma-resistant glass tubes, before and after sterilization In general, the integration of an optical path with the existing electric wiring can be done using two basic approaches:

The first one is to provide an optical path by a waveguide which is installed in parallel to the electric wiring, also in parallel to the sensor central axis, e.g. by providing access for an optical waveguide through the connector system of the electrode (FIG. 1, 102).

In the second approach, the optical path approaches the sensor at an angle or preferably from a perpendicular direction to the sensor central axis and features an optical waveguide integrated in the pH sensor (FIG. 2/3, arrow). This integrated waveguide (205, 211) realises the optical connection along the sensor central axis to a point in the vicinity of the pH sensitive glass membrane (210) where the optical chemical and/or physical sensor (208, 212) is preferably located. The second approach has the advantage that the electrical connector (201) does not require any modification and that the optical path is more independent of the electrical connections inside the sensor. The optical connection between the waveguide from the measurement electronics and the waveguide integrated in the pH electrode (205, 211) can be established without establishing a physical contact between the two elements. They even could be separated by an optional transparent element, e.g. for protection purposes. For a reliable optical connection, a good geometric alignment to the waveguide integrated with the pH electrode and a light beam focused via a suitable exit optical element is sufficient. Alternatively, depending on the availability of sufficient space in the bioprocess equipment design, the measurement electronics or light source or both of these could be mounted in direct alignment to the optical waveguide integrated in the electrode. FIG. 2a shows an alternative placement of the optical sensor (212).

In a further embodiment, it is possible to realise the optical waveguide integrated in the electrode by using a glass part of the pH electrode itself, e.g. the outer shaft glass (FIG. 3, 305). There may be a need for modifications in terms of cladding and protection from straylight (303/304), however, the main criterion for successful usage of a glass component of the sensor is the ability to detect the fluorescent response signal from the optical chemical and/or physical sensor (307) in a sufficiently large amplitude and with a sufficient amplitude difference from possible stray light sources. The coupling of light into the shaft glass (305) may be assisted by focusing the light using lenses or other optical elements. Typically, these optical elements are not part of the electrode itself but part of the delivering optics (not shown on figures for clarity).

Another embodiment includes the introduction of a 3-chamber electrode as shown in FIG. 4. The pH glass membrane (414) can be part of the glass tubing, leaving the space around the centre axis of the electrode for the optical assembly. The optical sensor (416) is attached to the bottom of the electrode, the optical waveguide (405) is installed along the centre axis. The innermost chamber (410) has access to the outside of the electrode by a series of openings (406) through the outlying chambers. This technology is known in the art, see e.g. DE 44 38 523. This arrangement optionally allows having a displaceable waveguide which could be removed from the electrode when subjecting the electrode to the sterilisation process of choice. In this case, a waveguide not compatible to the sterilisation process of choice can be utilised. It also has to be noted that the compartment (406-410) has no direct contact to the sample side of the electrode. Thus, this compartment does not necessarily need to remain sterile as long as it is placed outside the sterile area which further facilitates the handling of the sterilised sensor and the insertion of the optical waveguide. Of course, the displaceability of the waveguide is applicable independently from the installation along the centre axis, as the person of routine skill in the art will readily appreciate.

With advanced integration of optical elements it is possible to integrate the light source and means for detection into the sensor head as shown schematically in FIG. 5. This has the advantage that the sensor has electrical connections (501) only and that for instance a multipin connector can be used. The waveguide (505) can consist of a very simple straight construction without the need for guiding light around corners etc. If miniaturised properly, it is also feasible to integrate the whole read-out opto-electronics (504) in which case only electrical power and data are exchanged across the connector (501, 502).

It has to be noted that for all examples of embodiments, the lightwave geometries are exchangeable. For instance it is obvious that e.g. the 90° optical access methods as shown in FIG. 2 or the waveguide leaving through the sensor head assembly in FIG. 1 could also be used in the case of the central waveguide from FIG. 4 and vice versa. The specific choice of waveguide setup will depend on various parameters. To name a few, it will among other factors depend on the space requirements in a specific application, on the preferred method of sterilisation, on the placement of the light source etc. On the figures, liquid junctions are depicted as ceramic pin diaphragms. However, it is to be stressed that there are various other constructions of liquid junctions that could be chosen instead of a ceramic pin. Again, the proper choice will depend on the application and the chemical composition of the bioprocess solutions to be analysed.

FIG. 6 illustrates the absorption spectra of two gamma-resistant glass tubes of 0.9 mm wall thickness, usable in the context of the present invention. Tube A was measured as is, tube B was subjected to a gamma irradiation dose of 46-49 kGy. The absorbance is defined as $-\lg(I/I_0)$, as outlined in Skoog, Leary, "Instrumentelle Analytik", Springer Berlin, 1996, $4^{th}$ ed in German, p. 134-136. Forming the difference of the absorbances Abs(B)−Abs(A) yields a value close to 0 in the wavelength window of 400 nm to 600 nm.

The invention claimed is:

1. A combined electrode, comprising
   I) a glass pH electrode for measuring the pH of an analyte; and
   ii) an optical sensor for measuring a physical and/or chemical property of an analyte, wherein the physical and/or chemical property is not the pH; wherein said electrode is sterilizable without significant alteration of the optical characteristics of an optical input- and output paths to and from the optical sensor; and the optical sensor itself.

2. The combined electrode of claim 1, wherein the said optical characteristics is the spectrum in the range of 200 nm to 800 nm.

3. The combined electrode of claim 1, wherein the optical sensor is mounted on the outside of the electrode shaft.

4. The combined electrode of claim 3, wherein the optical sensor is mounted on lower third of the electrode shaft.

5. The combined electrode of claim 1, wherein the optical input- and output paths to and from the optical sensor comprise an optical waveguide, functionally connected or connectable to the optical sensor.

6. The combined electrode of claim 5, wherein the optical waveguide is integrated in the electrode shaft.

7. The combined electrode of anyone of claims 5, wherein the optical waveguide is displaceable from the combined electrode.

8. The combined electrode of claim 1, wherein said electrode is sterilizable by I) steam sterilisation sterilization; and/or ii) chemical sterilisation sterilization; and/or iii) irradiation sterilisation sterilization;

without significant alteration of the optical characteristics in the optical paths of and/or to the optical sensor.

9. The combined electrode of claim 1, wherein the electrode is sterilizable by irradiation sterilization chosen from the group consisting of gamma ray irradiation, electron beam processing, treatment with X-ray, treatment with UV light, and combinations thereof; without significant alteration of the optical characteristics in the optical paths of and/or to the optical sensor.

10. The combined electrode of claim 1, wherein the electrode is sterilizable by treatment with gamma rays without significant alteration of the optical characteristics in the optical paths of and/or to the optical sensor.

11. The combined electrode of claim 1, wherein the optical input- and/or output paths to and from the optical sensor is made from or comprises a glass material.

12. The combined electrode of claim 1, wherein the glass of the electrode is or comprises a borosilicate glass containing cerium.

13. A bioreactor or a bioprocess container, equipped with an combined electrode according to claim 1.

14. A method of determining the pH and yet another physical and/or chemical property of an analyte, said method comprising steps of I) providing a bioreactor or a bioprocess container according to claim 13, ii) sterilizing the bioreactor or bioprocess container of step I), iii) providing an analyte in said bioreactor or bioprocess container of step ii), and iv) determining the pH and another physical and/or chemical property of said analyte with said combined electrode.

15. The combined electrode of claim 1, wherein the said optical characteristics is the spectrum in the range of 350 nm to 700 nm.

16. The combined electrode of claim 1, wherein the said optical characteristics is the spectrum in the range of 400 nm to 600 nm.

17. A method of manufacturing a combined electrode according to claim 1, comprising steps of I) manufacturing and/or ii) obtaining optical input- and output paths to and from an optical sensor of the combined electrode of a material that is sterilizable without significant alteration of the optical properties.

* * * * *